United States Patent [19]

Riess et al.

[11] Patent Number: 4,613,708
[45] Date of Patent: Sep. 23, 1986

[54] BRANCHED PERFLUOROALKYL-1,2-ETHENES, THEIR PREPARATION AND THEIR USE AS OXYGEN CARRIERS

[75] Inventors: Jean Riess, Falicon; Francois Jeanneaux; Maurice Le Blanc, both of Nice; André Lantz, Vernaison, all of France

[73] Assignee: Produits Chemiques Ugine Kuhlmann, Paris, France

[21] Appl. No.: 467,648

[22] Filed: Feb. 18, 1983

[30] Foreign Application Priority Data

Mar. 26, 1982 [FR] France ............................ 82 05165

[51] Int. Cl.[4] ........................................... C07C 21/18
[52] U.S. Cl. ................................. 570/136; 570/155; 514/832; 514/833
[58] Field of Search ............... 570/136, 155; 514/759, 514/832, 833, 744

[56] References Cited

U.S. PATENT DOCUMENTS 3,962,439  6/1976  Yokoyama et al. .................. 514/832
3,989,843  11/1976  Chabert et al. ...................... 514/833

OTHER PUBLICATIONS

Synthesis de Tetrakis(Perfluoroalkyl)-1,2-Iodoethenes en Presence de Cuivre: Une Nouvelle Serie de Transporteurs de Gas Dissous pour Usages Biologiques.
The Reactions of Perfluoroalkyl Copper Compounds with 1-Bromo-1-Perfluoroalkylethylenes.

*Primary Examiner*—Natalie Trousof
*Assistant Examiner*—Joseph A. Boska
*Attorney, Agent, or Firm*—Pennie & Edmonds

[57] ABSTRACT

This invention concerns new branched perfluoroalkylated ethenes, their preparation and their use, in the form of aqueous emulsions, as oxygen carriers, and in particular as blood substitutes or as perfusion agents for the preservation of organs before transplant.

20 Claims, No Drawings

BRANCHED PERFLUOROALKYL-1,2-ETHENES, THEIR PREPARATION AND THEIR USE AS OXYGEN CARRIERS

TECHNICAL FIELD

This invention concerns new branched perfluoroalkylated ethenes, their preparation and their use, in the form of aqueous emulsions, as oxygen carriers, and in particular as blood substitutes or as perfusion agents for the preservation of organs before transplant.

BACKGROUND OF THE INVENTION

Perfluoroalkylated ethenes containing only straight perfluorinated chains are known, notably, from the published work of G. Santini, M. LeBlanc and J. G. Riess, TETRAHEDRON 29, 2411 (1973), and of F. Jeanneaux, G. Santini, M. Le Blanc, A. Cambon and J. G. Riess, TETRAHEDRON 30, 4197 (1974). The prior art does not, to applicants' knowledge, record perfluoroalkylated ethenes containing branched fluorinated alkyl chains.

The use of perfluorinated or highly fluorinated compounds as oxygen carriers or respiratory gases in blood substitutes has previously been the subject of numerous articles. A review of this subject was published by J. G. Riess and M. Le Blanc in ANGEWANDTE CHEMIE, INTERNATIONAL EDITION IN ENGLISH, 17, 621–700 (1978).

For a blood substitute to be considered entirely satisfactory, it must simultaneously fulfill five conditions:

- be obtainable in pure state and in a perfectly defined form;
- possess a high capacity for dissolving respiratory gases;
- be inert and atoxic;
- be capable of forming stable aqueous emulsions of oil in water type, with an average particle size of less than about 0.1 μm, with no particle exceeding 0.6 μm;
- be eliminable very rapidly from the organism.

None of the fluorinated carriers hitherto known fully satisfies all these conditions. The straight-chain bis-(perfluoroalkyl)-1,2-ethenes of the prior art, though already representing considerable progress from the purity standpoint, are always obtained in the form of mixtures of bis-cis- and trans-isomers, the latter being predominant. Thus, chromatographic analysis of the bis-(perfluoro-n-hexyl)-1,2-ethene or dihydro-7,8-perfluorotetradecene-7 shows that it contains 94.1% trans-isomer and 4.6% cis-isomer, the rest consisting mainly of the corresponding saturated derivative, bis-(perfluoro-n-hexyl)-1,2ethane. The cis- and trans-isomers of the straight chained bis-(perfluoroalkyl)-1,2-ethenes have boiling points so close together that it is difficult to separate the isomers by distillation. The differences in their boiling points are, however, distinct enough to entail differences in the rates of excretion of the isomers.

DISCLOSURE OF THE INVENTION

The new perfluoroalkylated ethenes of this invention, are trans-isomers of bis-(perfluoroalkyl)-1,2-ethenes having the general formula:

$$R_F-CH=CH-R'_F$$

in which $R_F$ and $R'_F$ represent $C_nF_{2n+1}$ radicals, at least one of which is branched. The value of n ranges from 3 to 20 for the branched chain groups and from 1 to 20 for the straight chain groups.

The applicants discovered, quite unexpectedly, that the usual reactions of formation of bis-(perfluoroalkyl)-1,2-ethenes, when at least one of the perfluoroalkylated groups is branched, yield in the majority of cases the trans-isomer exclusively, and in all cases more than 99.7% trans-isomer.

The branched bis-(perfluoroalkyl)-1,2-ethenes can be prepared by either the addition of an $R_FI$ perfluoroalkyl iodide to an $R'_FI3$ $CH=CH_2$ mono-(perfluoroalkyl)-ethene, followed by a dehydroiodination by a base, which can be written

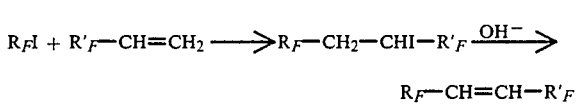

or by the reaction of an $R_FI$ perfluoroalkyl iodide with an $R'_F-CBr=CH_2$ bromo-1-perfluoroalkyl-1-ethene in the presence of copper, in a solvent like dimethylformamide, which can be written

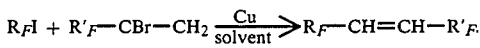

For preparation of the compounds according to the invention, the branched perfluorinated alkyl chain can be carried by just one of the reactants of the above-mentioned reactions or by both reactants at the same time. In all cases, the trans-isomer of the bis-(perfluoroalkyl)-1,2-ethene is exclusively obtained, or at least a mixture containing more than 99.7% trans-isomer. The $R_F$ and $R'_F$ groups can have the same number of atoms, carbon or a different number of carbon atoms.

The compounds according to the invention are liquid, have low vapor pressure, and very low surface tensions. They are as harmless as the corresponding straight derivatives and possess at least an equal dissolving capacity for oxygen. Thus, 100 ml of perfluoroisopropyl-1-perfluoro-n-hexyl-2-ethene for formula:

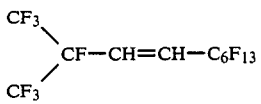

dissolve up to 50 ml of oxygen at 37° C. under a pressure of 760 mm of mercury (101.325 kPa).

The applicants also unexpectedly discovered that the branched compounds of this invention, are distinguished from the corresponding straight compounds by their capacity to yield more stable aqueous emulsions and also have a greater rate of elimination from the organism at the same time.

The emulsions, which are very stable and very fine in water or in a physiological saline, whether artificial or not, are easily prepared by using ethylene oxide and propylene oxide condensates as surface-active agents, such as the product marketed by PCUK Produits Chimiques Ugine Kuhlmann under the registered trademark PLUORONIC F-68. Other surface-active agents, such as egg yolk or soybean lecithins, or mixtures of these compounds and fluorinated-chain surfactants, or any other adequate surface-active agent can also be used. The dispersion of the compound of this invention, in water or in physiological saline is carried out by known means, e.g., by means of a homogenizer under pressure or by ultrasonic methods. Thermodynamically stable microemulsions can also be obtained by using a suitable combination of surface-active agents as would be apparent to those skilled in the art.

The following examples illustrate the preparation of the compounds according to the invention and the preparation of aqueous emulsions containing those products.

EXAMPLE 1

Preparation of trans-bis-(perfluoroisopropyl)-1,2-ethene

A mixture of 764 g of perfluoroisopropyl-1-ethene (3.9 moles) and 2,370 g of iodo-2-perfluoropropane (8 moles) is heated in an autoclave at 200° C. for 16 hours. The reaction mixture is cooled to 0° C. and then washed three times with a 10% weight aqueous potassium iodide solution. The organic phase is poured off, filtered on phase-separating paper and distilled. The excess iodo-1-perfluoroisopropane (1,250 g) is collected first, then an intermediate fraction of 120 g, consisting of a 50/50 by weight mixture of bis-(perfluoroisopropyl)-1,2-ethene and bis-(perfluoroisopropyl)-1,2-ethane, and finally 780 g of pure iodo-1-bis-(perfluoroisopropyl)-1,2-ethene, passing at 41° C. under 15 mm of mercury (1.999 kPa).

One slowly adds 170 g of this iodo-1-bis-(perfluoroisopropyl)-1,2-ethene (0.34 mole) to a solution of 17.4 g of potassium hydroxide in 250 ml of ethyl alcohol, cooled to 0° C. The mixture is stirred for one hour at room temperature. The potassium iodide formed is then filtered and 250 ml of water are added. The organic phase is poured off, filtered on phase separating paper and distilled. One collects 78 g of trans-bis-(perfluoroisopropyl)-1,2-ethene, boiling at 80° C. under 760 mm of mercury (101.325 kPa) and chromatographically pure.

EXAMPLE 2

Preparation of trans-perfluoroisopropyl-1-perfluoro-n-hexyl-2-ethene

A mixture of 1,730 g of perfluoro-n-hexyl-1-ethene (5 moles) and 2,960 g of iodo-2-perfluoropropane (10 moles) is heated for 20 hours at 190° C. in an autoclave. After cooling, the reaction products are washed three times with 200 ml of a 10% by weight aqueous potassium iodide solution. The organic phase poured off is filtered on phase separating paper and then distilled. One successively collects 1,200 g of iodo-2-perfluoropropane, passing to 25°-30° C. at atmospheric pressure, and then, under reduced pressure, 2,470 g of iodo-1-perfluorohexyl-1-perfluoroisopropyl-2-ethane, distilling at 75° C. under 15 mm of mercury (1.999 kPa). The residue (430 g) consists essentially of telomeres of formula:

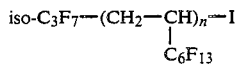

Over a period of two to three hours, 2,026 g of iodo-1-perfluorohexyl-1-perfluoroisopropyl-2-ethane (3.16 moles) are added drop by drop to 221 g of a 10% by weight alcoholic potassium hydroxide solution, stirred and cooled to 0° C. Stirring is then continued for two hours at room temperature. The potassium iodide precipitate is filtered and is washed three times with 100 ml of ethanol. Two liters of distilled water are added and the organic phase is separated. It is filtered on phase separating paper and is distilled under reduced pressure. One collects 1,540 g of trans-perfluoroisopropyl-1-perfluoro-n-hexyl-2-ethene, boiling at 67° C. under 20 mm of mercury (2.666 kPa) and chromatographically pure.

EXAMPLE 3

Preparation of trans-perfluoroisopropyl-1-perfluoro-n-hexyl-2-ethene

A mixture of 5 g of perfluoroisopropyl-1-ethene (25.5 millimoles) and 23.8 g of iodo-1-perfluorohexane (51.1 millimoles) is heated in a sealed 300 ml flask at 195° C. for 48 hours. The mixture is then brought to room temperature and washed with 20 ml of a 10% by weight aqueous potassium iodide solution. The perfluorinated phase is poured off, filtered on phase separating paper and then distilled. One collects at 90° C., under 20 mm of mercury (2.666 kPa), 3.85 g of iodo-1-perfluorosiopropyl-1perfluoro-hexyl-2-ethane.

This intermediate product undergoes dehydroiodination with an alcoholic potassium hydroxide solution under conditions identical to those used in Example 2 for dehydroiodination of the iodo-1-perfluorohexyl-1-perfluoroisopropyl-2-ethane isomer. Chromatographically pure trans-perfluoroisopropyl-1-perfluoro-n-hexyl-2-ethene is again obtained.

EXAMPLE 4

Preparation of a trans-perfluoroisopropyl-1-perfluoro-n-hexyl-2-ethene emulsion

A mixture of 1.5 ml (2.55 g) of trans-perfluoroisopropyl-1-perfluoro-n-hexyl-2-ethene and 8.5 ml of an aqueous solution containing 0.29 g of PLURONIC F-68 (PCUK registered trademark for an ethylene oxide and propylene oxide block copolymer) and 0.043 g of egg yolk lecithin is subjected to ultrasonic action in a SONIFIER B-30 BRANSON apparatus equipped with a probe 3 mm in diameter. After two ultrasonic irradiations of 30 seconds, an emulsion is obtained which passes totally through a MILLIPORE filter having calibrated pores 0.45 μm in diameter. The average size of the particles, measured by means of a NANOSIZER-COULTRONICS apparatus, is less than 0.3 μm. After one week of storage at room temperature, no sedimentation nor variation in size of particles is evident.

For purposes of comparison, an aqueous emulsion of bis-(perfluoro-n-butyl)-1,2-ethene is made under the same conditions. The size of the particles of that emulsion is similar to that of the previous emulsion, but on storage the formation of a sediment is evident at the end of one week.

We claim:

1. Trans-isomers of bis-(perfluoroalkyl)-1,2-ethenes having the general formula:

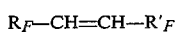

in which the $R_F$ and $R'_F$ groups represent $C_nF_{2n+1}$ radicals, at least one of which is branched, and where n ranges from 3 to 20 for the branched groups and from 1 to 20 for the straight groups.

2. Oil in water emulsions comprising the bis-(perfluoroalkyl)-1,2-ethenes of claim 1 as the oil phase.

3. A blood substitute comprising the oil-in-water emulsion of claim 2 having a particle size of less than about 0.6 millimicrons.

4. Trans isomers of bis-(perfluoroalkyl)-1,2-ethenes produced by:
   reacting a branched perfluoroalkyl iodide with a straight or branched mono-(perfluoroalkyl)-ethene to obtain an iodinated derivative of the branched bis-(perfluoroalkyl)-1,2-ethene; and
   dehydroiodinating the iodated derivative with an alkaline base to form trans isomers of bis-(perfluoroalkyl)-1,2-ethene, or
   reacting a straight or branched perfluoroalkyl iodide with a branched mono-(perfluoroalkyl)-ethene to form the iodinated derivative thereof, and
   dehydroiodinating the iodated derivative with an alkaline base to form branched bis-(perfluoroalkyl)-1,2-ethene.

5. Trans isomers of perfluoroalkyl-1,2-ethenes produced by:
   reacting a branched perfluoroalkyl iodide with a straight or branched mono-(perfluoroalkyl)-ethene to obtain an iodinated derivative of the branched bis-(perfluoroalkyl)-1,2-ethene; and
   dehydroiodinating the iodated derivative with an alkaline base to form trans isomers of bis-(perfluoroalkyl)-1,2-ethene, or
   reacting a straight or branched perfluoroalkyl iodide with a branched mono-(perfluoroalkyl)-ethene to form the iodinated derivative thereof, and
   dehydroiodinating the iodated derivative with an alkaline base to form branched bis-(perfluoroalkyl)-1,2-ethene.

6. Oil-in-water emulsions comprising the bis-(perfluoroalkyl)-1,2-ethenes of claim 4 as the oil phase.

7. A blood substitute comprising oil-in-water emulsions of claim 6 having a particle size of the less than 0.6 millimicrons.

8. Oil-in-water emulsions comprising the perfluoroalkyl-1,2-ethenes of claim 5 as the oil phase.

9. A blood substitute comprising the oil-in-water emulsions of claim 8 having a particle size of the less than 0.6 millimicrons.

10. The trans-bis perfluoroisopropyl-1,2-ethene of claim 4.

11. The trans perfluoroisopropyl-1-perfluoro-n-hexyl-2-ethene of claim 5.

12. The oil-in-water emulsions of claim 2 wherein the water phase comprises water or physiological saline.

13. The oil-in-water emulsions of claim 6 wherein the water phase comprises water or physiological saline.

14. The oil-in-water emulsions of claim 8 wherein the water phase comprises water or physiological saline.

15. The oil-in-water emulsions of claim 12 further comprising a surface active agent of an ethylene oxide and propylene oxide condenstate, a fluorinated-chain surfactant, an egg yolk or soybean lecithin, or a mixture of these compounds.

16. The oil-in-water emulsions of claim 13 further comprising a surface active agent of an ethylene oxide and propylene oxide condenstate, a fluorinated-chain surfactant, an egg yolk or soybean lecithin, or a mixture of these compounds.

17. The oil-in-water emulsions of claim 15 further comprising a surface active agent of an ethylene oxide and propylene oxide condenstate, a fluorinated-chain surfactant, an egg yolk or soybean lecithin, or a mixture of these compounds.

18. Trans-isomers of perfluoroalkyl-1,2-ethenes having the general formula:

$$R_F-CH=CH\ R'_F$$

in which the $R_F$ and $R'_F$ groups represent $C_nF_{2n+1}$ radicals, at least one of which is branched, and where n ranges from 3 to 20 for the branched groups and from 1 to 20 for the straight groups.

19. Oil-in-water emulsions comprising the perfluoroalkyl-1,2-ethenes of claim 18 as the oil phase.

20. A blood substitute comprising the oil-in-water emulsion of claim 19 having a particle size of less than about 0.6 millimicrons.

* * * * *